US012588917B2

(12) United States Patent
Lefauconnier

(10) Patent No.: US 12,588,917 B2
(45) Date of Patent: Mar. 31, 2026

(54) PEDICLE MARKER

(71) Applicant: Neo Medical SA, La Villette (CH)

(72) Inventor: Vincent Lefauconnier, Brent (CH)

(73) Assignee: NEO MEDICAL S.A., La Villette (CH)

( * ) Notice: Subject to any disclaimer, the term of this patent is extended or adjusted under 35 U.S.C. 154(b) by 705 days.

(21) Appl. No.: 16/972,058

(22) PCT Filed: Jun. 17, 2019

(86) PCT No.: PCT/IB2019/055041
§ 371 (c)(1),
(2) Date: Dec. 4, 2020

(87) PCT Pub. No.: WO2019/229391
PCT Pub. Date: Dec. 19, 2019

(65) Prior Publication Data
US 2021/0169506 A1     Jun. 10, 2021

(30) Foreign Application Priority Data

Jun. 15, 2018     (WO) .................. PCT/IB2018/054426

(51) Int. Cl.
*A61B 17/17*          (2006.01)
*A61B 17/68*          (2006.01)
(Continued)

(52) U.S. Cl.
CPC ........ *A61B 17/1757* (2013.01); *A61B 17/708* (2013.01); *A61B 17/848* (2013.01);
(Continued)

(58) Field of Classification Search
CPC . A61B 17/1757; A61B 17/708; A61B 17/848; A61B 17/88; A61B 90/39;
(Continued)

(56) References Cited

U.S. PATENT DOCUMENTS

| | | | |
|---|---|---|---|
| 5,800,439 A | 9/1998 | Clyburn |
| 6,175,758 B1 | 1/2001 | Kambin |
(Continued)

FOREIGN PATENT DOCUMENTS

| | | |
|---|---|---|
| CN | 101336094 A | 12/2008 |
| CN | 101511288 A | 8/2009 |
(Continued)

OTHER PUBLICATIONS

International Search Report dated Oct. 24, 2019 for Application No. PCT/IB2019/055041.
(Continued)

*Primary Examiner* — Tracy L Kamikawa
(74) *Attorney, Agent, or Firm* — NIXON & VANDERHYE

(57) ABSTRACT
The present invention concerns a pedicle marker (1) including an elongated tubular body (3) comprising a proximal end (5) for receiving a guide-wire (GW) and a distal end (7) through which the Kirschner-wire can exit, wherein the elongated tubular body extends from the proximal end to the distal end; and a plug (9) enclosing the elongated tubular body, the plug being located between the proximal end and the distal end. The elongated tubular body includes a non-threaded external surface extending at least from the plug to the distal end.

17 Claims, 7 Drawing Sheets

(51) Int. Cl.

| | |
|---|---|
| *A61B 17/70* | (2006.01) |
| *A61B 17/84* | (2006.01) |
| *A61B 17/88* | (2006.01) |
| *A61B 17/90* | (2006.01) |
| *A61B 90/00* | (2016.01) |

(52) U.S. Cl.
CPC .............. *A61B 17/88* (2013.01); *A61B 90/39* (2016.02); *A61B 17/90* (2021.08); *A61B 2090/3916* (2016.02)

(58) Field of Classification Search
CPC .... A61B 2090/3916; A61B 2017/3441; A61B 2017/3419; A61B 2017/3482
See application file for complete search history.

(56) References Cited

U.S. PATENT DOCUMENTS

| | | | | |
|---|---|---|---|---|
| 6,565,572 | B2 * | 5/2003 | Chappius | A61B 17/7092 600/300 |
| 6,752,833 | B2 * | 6/2004 | Hesseling | A61L 31/06 623/23.48 |
| 7,244,241 | B2 * | 7/2007 | Gross | A61F 2/4612 604/35 |
| 8,152,837 | B2 | 4/2012 | Altarac et al. | |
| 8,388,623 | B2 * | 3/2013 | Browne | A61B 17/1604 606/186 |
| 8,425,532 | B2 * | 4/2013 | Flom | A61B 17/3423 606/104 |
| 8,545,531 | B2 * | 10/2013 | Geist | A61B 17/848 606/198 |
| 9,339,294 | B2 * | 5/2016 | Mandeen | A61B 17/1764 |

| | | | | |
|---|---|---|---|---|
| 2001/0021852 | A1 | 9/2001 | Chappius | |
| 2002/0058946 | A1 | 5/2002 | Gross | |
| 2006/0085008 | A1 | 4/2006 | Jäggi et al. | |
| 2007/0016219 | A1 * | 1/2007 | Levine | A61B 90/39 606/99 |
| 2007/0093846 | A1 | 4/2007 | Frigg et al. | |
| 2007/0255287 | A1 | 11/2007 | Rabiner | |
| 2008/0021480 | A1 | 1/2008 | Chin et al. | |
| 2008/0077136 | A1 | 3/2008 | Triplett et al. | |
| 2010/0331893 | A1 | 12/2010 | Geist et al. | |
| 2018/0153585 | A1 * | 6/2018 | Levine | A61B 17/0206 |

FOREIGN PATENT DOCUMENTS

| | | |
|---|---|---|
| CN | 108078622 A | 5/2018 |
| JP | 2004501716 A | 1/2004 |
| JP | 2009544361 A | 12/2009 |
| WO | 2008011495 A2 | 1/2008 |
| WO | 2011053589 A2 | 5/2011 |

OTHER PUBLICATIONS

Written Opinion of the ISA dated Oct. 24, 2019 for Application No. PCT/IB2019/055041.

Office Action issued in Indian Patent Application No. 202017054088 dated Oct. 10, 2022.

Office Action issued in Chinese Patent Application No. 201980039523.8 dated Oct. 23, 2023.

Office Action issued in Japanese Patent Application No. 2020-565960 dated May 30, 2023.

Office Action, issued in Chinese Patent Application No. 201980039523.8 dated May 23, 2024.

* cited by examiner

PEDICLE MARKER

CROSS-REFERENCE TO RELATED APPLICATIONS

The present application is a United States national stage application of International Patent Application No. PCT/IB2019/055041 filed on Jun. 17, 2019 designating the United States, and claims foreign priority to International Patent Application No. PCT/IB2018/054426 filed on Jun. 15, 2018 the contents of both documents being herewith incorporated by reference in their entirety.

FIELD OF THE INVENTION

The present invention concerns a pedicle marker, a pedicle guide-wire marker or a Kirschner-wire marker. The device can be inserted into a passage formed in a vertebra or pedicle, for example a pedicle of a vertebral arch, to mark the location of the passage formed in the vertebra or pedicle.

The device can also be used for handling or manipulating the vertebra, for example, to displace the vertebra to permit the insertion or adjustment of a spine cage inserted for spinal fusion between two or more vertebrae of the spine.

BACKGROUND

Spinal screws in association with an orthopaedic rod are used to correct spinal deformity or to treat spinal trauma. An orthopaedic rod is placed and held in the heads of a plurality of spinal screws implanted in vertebrae so as to treat a degenerative spine, correct a spinal deformity or to treat a spinal trauma. Prior to the insertion of the spinal screws into vertebrae, a passage or bore for receiving the shaft of a spinal screw is formed in the pedicle or vertebra using a succession of drilling tools such as tap, awl, pedicle finder, probe.

A thin guide wire such as Kirschner-wire (or K-wire) can be placed in each of the passages or bores to guide the spinal screw into the passage or bore for insertion into the pedicle or vertebra. The shaft of the spinal screw typically includes a through-bore through which the guide wire is passed allowing the screw to be guided to the passage or bore formed in the pedicle.

However, multiple pedicle screws are often required in a plurality of vertebrae meaning that, prior to insertion of the pedicle screws in the vertebrae, multiple passages or bores contain multiple K-wires of more than 40 cm in length extending outwards from the patient's spine and fills the space in which a surgeon must work with dangling guide wires that are free to swing around (for example, see FIG. 6).

This causes an obstruction for the surgeon limiting their range of motion and movements over the patient as well as hindering other actions carried out by the Surgeon prior to placement of the pedicle screws in the vertebra such as decompression, spinal release, discectomy or interbody cage placement.

In addition, displacement or re-positioning of one or more vertebra may be necessary to allow the insertion of a spine cage inserted for spinal fusion between two or more vertebrae of the spine. This spine cage insertion is carried out using a tool called a spine cage holder but this action is obstructed by the presence of multiple dangling guide wires in the area in which the Surgeon is working and often made difficult by narrow entry linked to the collapsed degenerated disc.

SUMMARY

The goal of the present invention is to provide a pedicle marker that overcomes the above-mentioned inconvenience. In particular, the goal of the present invention is to assure that a Surgeon can carry out their role without being obstructed.

The present invention addresses the above-mentioned limitations by providing a pedicle marker including:

an elongated tubular body comprising a proximal end for receiving a guide-wire or Kirschner-wire and a distal end through which the Kirschner-wire can exit, wherein the elongated tubular body extends from the proximal end to the distal end; and a plug enclosing the elongated tubular body, the plug being located between the proximal end and the distal end;

wherein the elongated tubular body includes a non-threaded external surface extending at least from the plug to the distal end.

The pedicle marker according to the present invention advantageously allows the passages or bores for receiving the shaft of a spinal screw that are formed in the pedicle or vertebra using a drilling tool or tap to be marked and distinguished without causing obstruction for the surgeon while simultaneously allowing the Surgeon to carry out other required actions such as displacement or re-positioning of one or more vertebra to allow, for example, insertion of a spine cage.

The pedicle marker also allows the K-wire to be inserted into the passage or bore without bending of the K-wire. The pedicle marker further permits removal of the pedicle marker without bending of the K-wire and without simultaneously pulling out the k-wire.

Moreover, the pedicle markers of the present disclosure do not disrupt the Surgeon's current manner of operating on a patient but simply bring an additional option that renders the operation easier for the Surgeon.

This allows the Surgeon to work more efficiently and more quickly permitting the duration of the operation to be reduced for the patient.

The present invention also concerns a kit of instruments including at least one or a plurality of the above-mentioned pedicle markers. They can be provided sterile and for single use or could be re-sterilized in the Hospital.

The present invention also concerns an orthopaedic method.

Other advantageous features can be found in the dependent claims.

The above and other objects, features and advantages of the present invention and the manner of realizing them will become more apparent, and the invention itself will best be understood from a study of the following description with reference to the attached drawings showing some preferred embodiments of the invention.

A BRIEF DESCRIPTION OF THE SEVERAL VIEWS OF THE DRAWINGS

Herein, identical reference numerals are used, where possible, to designate identical elements that are common to the Figures.

DETAILED DESCRIPTION OF THE SEVERAL EMBODIMENTS

Figure 1A:
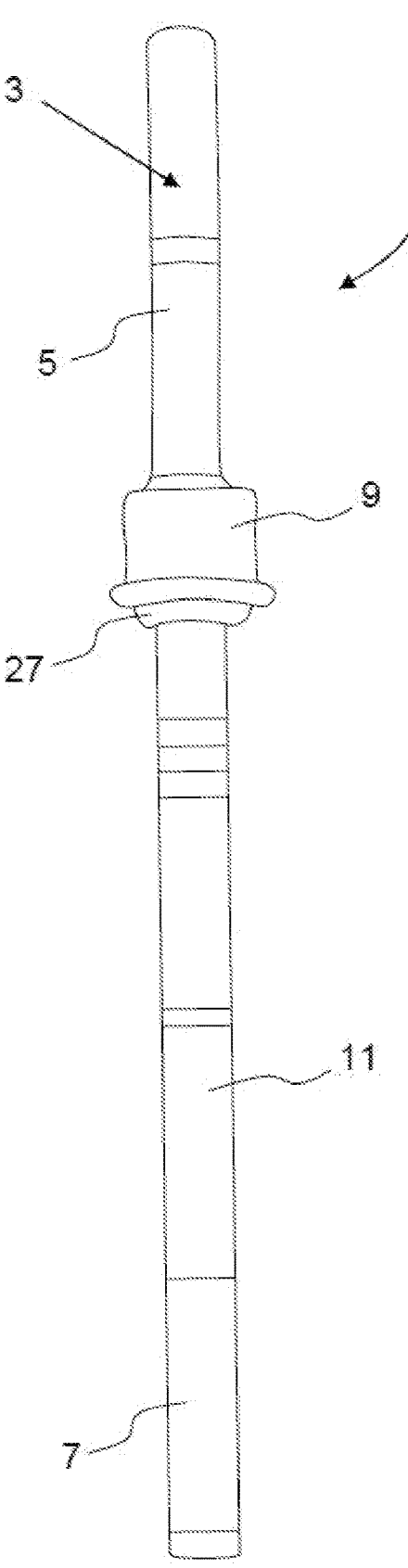
FIGS. 1A to 1F show non-limiting and exemplary embodiments of a pedicle marker of the present disclosure.
Figures 1B, 1C, 1D, 1E, 1F:
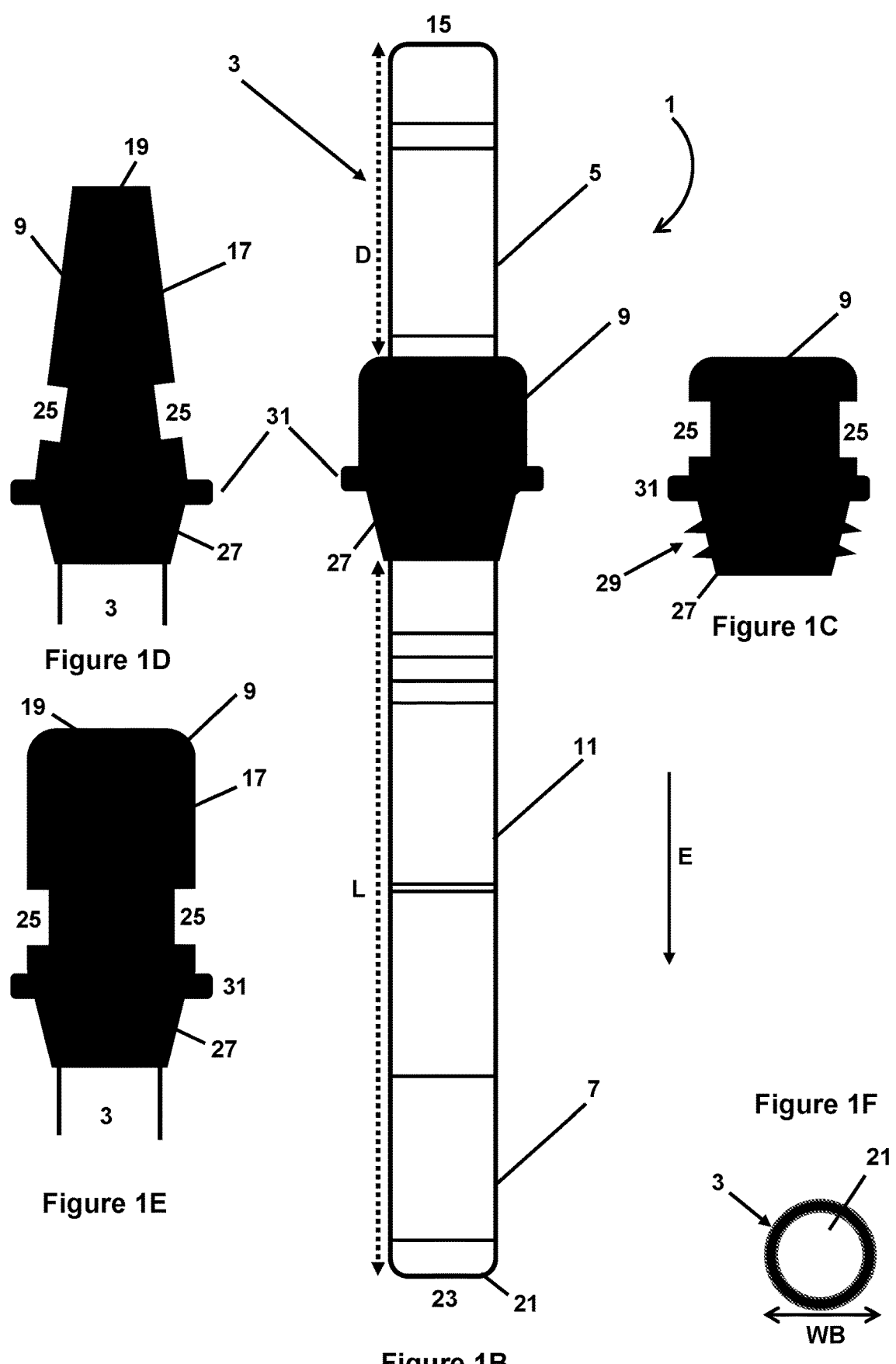

An exemplary pedicle marker or pedicle guide-wire marker 1 according to the present disclosure is shown, for example, in FIGS. 1A and 1B.

The pedicle marker 1 includes an elongated tubular body 3 comprising a proximal end 5 (end closest to a Surgeon when in use) for receiving a guide wire or Kirschner-wire GW and a distal end 7 through which the Kirschner-wire can exit. The elongated tubular body 3 extends from the proximal end 5 to the distal end 7.

The guide wire or Kirschner-wire or K-wire GW typically have a diameter between 0.9 and 1.5 mm and a length of approximately 40 cm. The wire is typically a solid elongated metal wire for example comprising or consisting of stainless steel. However, larger diameters are also possible.

The elongated tubular body 3 delimits a passage 21 (see for example FIG. 1F) configured to receive the guide wire or Kirschner-wire GW and through which the wire can, for example, fully pass through from one side to the other. The passage 21 extends from an outer extremity 15 of the proximal end 5 to an outer extremity 23 of the distal end 7. The passage 21 extends completely through the body 3.

The passage 21 has, for example, a complementary shape to that of the guide-wire, for example, permitting the guide-wire GW to be received (for example, snuggly received) and guided through the elongated tubular body 3 from the proximal end 5 to the distal end 7.

The passage 21 may, for example, define (substantially) a hollow cylindrical shape and the guide-wire GW may for example define a cylindrical shape of smaller diameter permitting the guide-wire GW to be received and guided through the elongated tubular body 3. The passage 21 and the guide-wire GW may however define other shapes and are not limited to a cylindrical shape or profile.

The elongated tubular body 3 may comprise or consist solely of a metal, for example aluminum or stainless steel; or of a polymer or plastic material for example polyamide, or polyetherimide, or polysulfone, or a member of the PAEK family, or the PEEK family or the PEKK family.

The elongated tubular body 3 has a width or outer diameter that is slightly smaller than a width or outer diameter of the bore or passage (for example, an elongated bore or elongated open passage) to be formed in the pedicle (for example a pedicle of a vertebral arch). This assures a snug fit in the bore or passage but also easily insertion and removal by the Surgeon. The width or diameter of the elongated tubular body 3 can be, for example, between 2 mm and 4 mm, for example, 3 mm.

The elongated tubular body 3 may, for example, have a full length between 4 cm and 8 cm, for example 6 cm. However, other lengths are also possible.

The pedicle marker 1 further includes a plug or holder 9 enclosing (or fulling enclosing or surrounding) the elongated tubular body 3. The plug 9 is located, for example, between the proximal end 5 and the distal end 7.

The plug 9 holds the elongated tubular body 3 and holds the pedicle marker 1 in the bore or passage.

Figure 2:
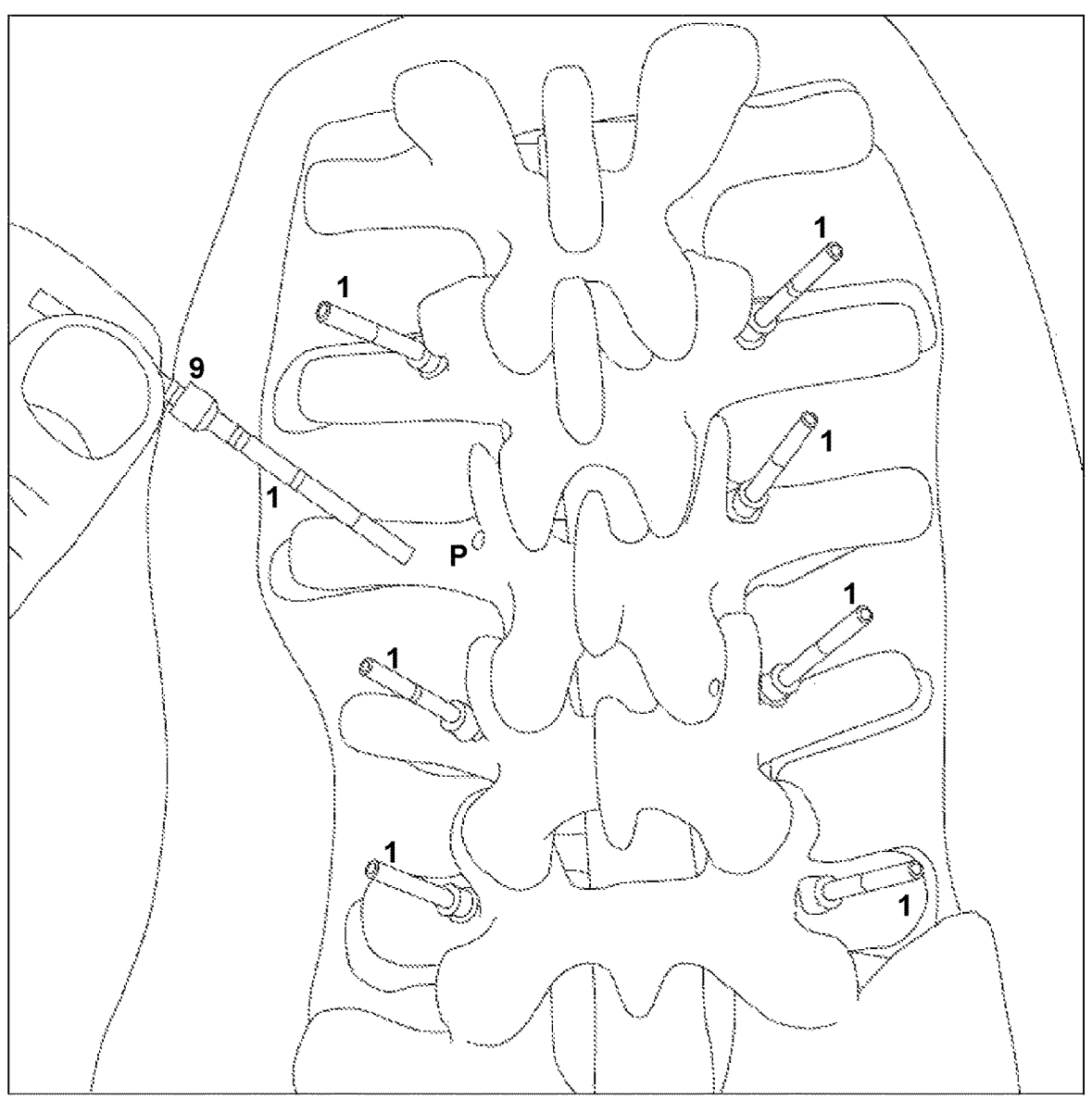
FIGS. 2 and 3 show a plurality of pedicle markers according to the present disclosure being positioned or positioned in pedicles or vertebrae.
Figure 3:
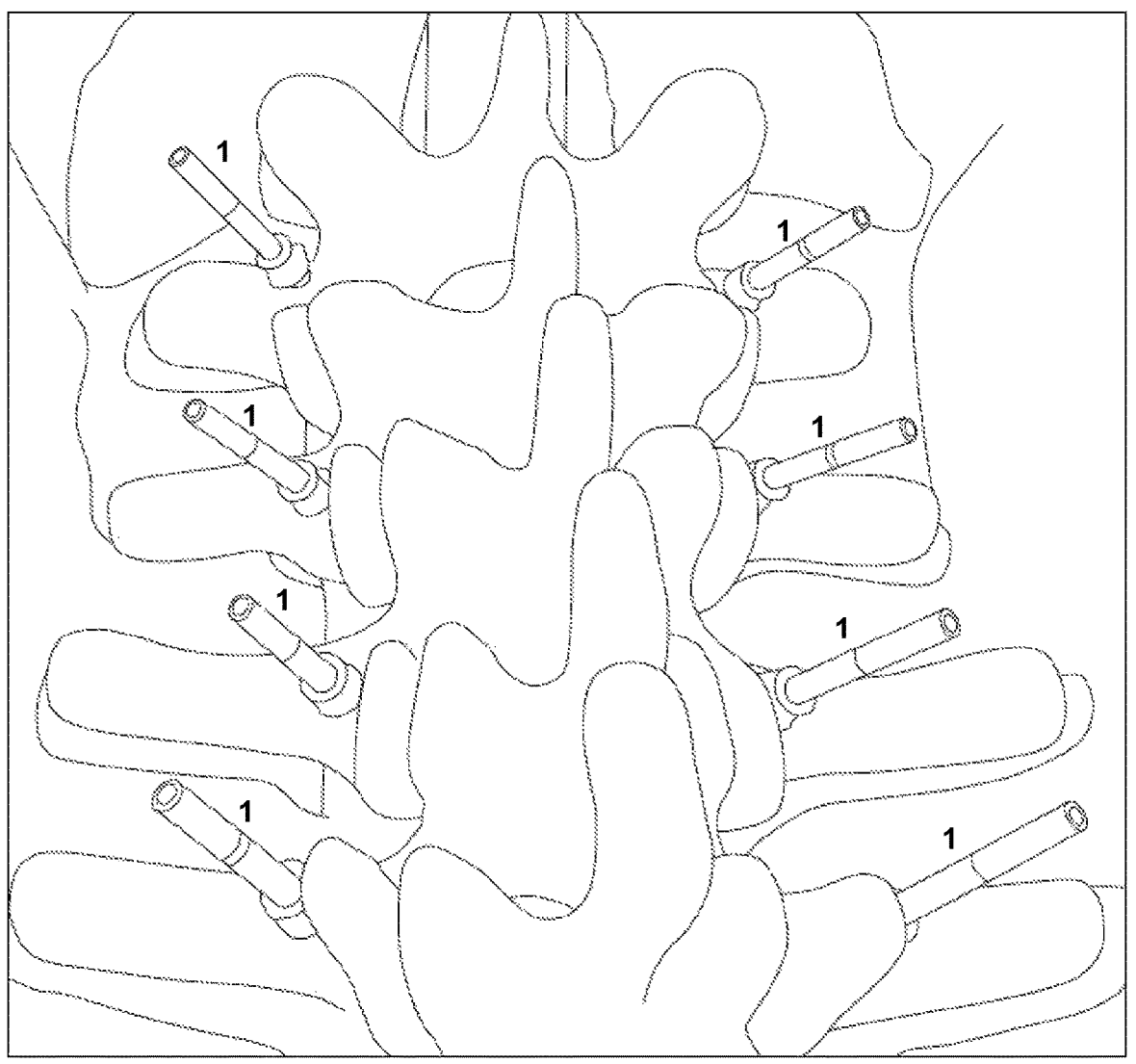

When placed in the passage or bore P in the vertebra or pedicle (see FIGS. 2 and 3), the plug 9 directly contacts the bone material at the entrance of the passage or bore to at least partially close or fully close the passage or bore P. The plug 9 comprises an outer surface that contacts an outer surface of the entrance of the passage or bore P so as to plug the passage or bore entrance. This advantageously prevents or minimizes blood flow out of the passage or bore P.

The plug 9 may comprise or consist solely of a metal, for example aluminum or stainless steel; or of a polymer or plastic material for example polyamide, or polyetherimide, or polysulfone, or a member of the PAEK family, or the PEEK family or the PEKK family.

The plug 9 is attached to the elongated tubular body 3 directly or indirectly and encircles the elongated tubular body 3. The plug 9 may, for example, be glued, welded or molded onto the elongated tubular body 3.

The plug 9 can be immobile on the elongated tubular body 3. Alternatively, the plug 9 is displaceable along the length of the elongated tubular body 3 and, for example, is maintained in position on the elongated tubular body 3 via for example a friction fit, or a press-fit.

The plug 9 defines a passage or channel in which the elongated tubular body 3 is located. The passage or channel may, for example, have an inner width or diameter larger or slightly larger than the outer width or diameter WB (FIG. 1F) of the elongated tubular body 3.

The passage or channel may, for example, have an inner width or diameter slightly larger than the outer width or diameter WB (FIG. 1F) of the elongated tubular body 3 to permit a friction fit or a press-fit of the plug 9 to the elongated tubular body 3.

The plug 9 can be located at a distance from both the proximal end 5 and the distal end 7.

The plug 9 can be located, for example, at a position that is between (i) the mid-length (location corresponding to half the length of the elongated body 3, the length extending in the extension direction E shown in FIG. 1B) of the elongated body 3 and (ii) the outer extremity of the proximal end 5. The plug 9 can be located, for example, at a position that is between the mid-length of the elongated body 3 and the outer extremity of the proximal end 5 and not at the outer extremity of the proximal end 5.

The plug 9 can be, for example, located or positioned on the elongated tubular body 3 at a distance D (for example, D can be between 0.1 cm and 2.5 cm, for example 2 cm) from the outer extremity 15 of the proximal end 5 (and/or at a distance L from the outer extremity 23 of the distal end 7).

Alternatively, the plug 9 can be located at the extremity 15 of the proximal end 5 (for example, at D=0). FIGS. 1D and 1E show non-limiting examples of such a plug 9 that is to be located at the extremity 15 of the proximal end 5.

The plug 9 includes an upper section 17 extending away from the proximal end 5 and from the extremity 15. The upper section 17 defines a channel 19 configured to receive and guide the guide-wire or Kirschner-wire GW. The upper section 17 can, for example, define a funnel for receiving and guiding the guide-wire GW as shown for example in FIG. 1D.

The plug 9 of any one of the embodiments may comprise a lower section 27 having a width or diameter permitting to seal or (at least partially) close the passage or bore P formed in the pedicle or vertebrae.

The width or diameter of the lower section 27 can, for example, be decreasing in the direction of the distal end 7, for example decreasing in a linear or non-linear manner in the direction of the distal end 7.

In other words, the width or diameter of the lower section 27 can, for example, be increase in the direction of the proximal end 5, for example increasing in a linear or non-linear manner in the direction of the proximal end 5. This provides a plurality or diameters or widths for sealing or closing the passage or bore P formed in the pedicle or vertebrae.

The plug 9 may, for example, comprise a downwardly sloped outer surface sloping downwards or inwards towards the body 3 in the direction of the distal end 7; or an upwardly sloped outer surface sloping upwards or outwards from the body 3 in the direction of the distal end 7.

The lower section 27 may, for example, define a funnel profile permitting to seal or close the passage or bore P formed in a pedicle or vertebrae.

The lower section 27 may alternatively or additionally include one or more flexible flaps or winglets 29 (see, for example, FIG. 1C) permitting to seal or close a passage formed in the pedicle or vertebrae.

The plug 9 may further include a landing 31 protruding or extending (for example, radially) outwards from the plug 9 or body 3. The landing 31 may for example define an annular protrusion encircling the body of the plug 9 and/or the body 3. The landing 31 define an intermediate section located between and interconnecting the lower section 27 and the upper section 17.

The lower section 27 extends to directly contact the landing 31. The landing 31 also assures that blood flow out of the bore or passage P in the pedicle is minimized or prevented, particularly when the bore or passage has been formed too wide and the lower section 27 is not sufficiently wide to seal or close the opening defined by the passage or bore P.

The landing 31 may, for example, define a protrusion that is (substantially) perpendicular to the body 3.

The plug 9 may comprise at least one groove or depression 25 configured to receive a surgical tool (FIGS. 1C, 1D, 1E). The groove or depression 25 may, for example, extend fully or partially around a body of the plug 9. The groove or depression 25 may be, for example, an annular groove or depression. This allows a tool such as a distractor (see FIG. 4) to press upon two pedicle markers to allow the pedicles/vertebrae to be displaced to a desired position, for example to allow facilitate the insertion or displacement of a spinal cage.

The elongated tubular body 3 includes, for example, a non-threaded external surface 11 extending at least from the plug 9 to the distal end 7, for example, from the lower extremity of the plug 9 to the outer extremity 23 along a length L of the elongated tubular body 3. The length L, for example, corresponds or matches a length of the threaded screw shaft of a pedicle screw.

The external surface 11 is a thread-less surface. The external surface 11 is a screw-thread-less surface.

The external surface 11 may, for example, comprise a flat or smooth outer surface or a surface without projections and/or depressions.

The external surface 11 may, for example, comprise at least one or a plurality of regions having a flat outer surface or a surface without projections and/or depressions. The majority of the area defined by the external surface 11 has a flat surface or a surface without projections and/or depressions.

This assures that the passage or bore P is not excessively widened or weakened by the marker 1 thus assuring a correct and solid gripping by the pedicle screw in the pedicle when it is eventually positioned in the same passage or bore P.

The elongated tubular body 3 may include a non-threaded external surface 11 along the entire length of the elongated tubular body 3, or along the entire length of the exposed outer surface 11 of the elongated tubular body 3.

The outer surface of the elongated tubular body 3 can, for example, be closed or sealed or hermetic or liquid-tight in the elongated direction of extension E of the elongated tubular body 3. The lateral surface of the elongated tubular body 3 is or defines a closed surface or an opening-less surface. For example, closed between at least the plug 9 and the distal end 7 or outer extremity 23. The external lateral surface 11 is or defines a closed or continuous surface or an opening-free surface. This assures that blood flow out of the bore or passage P in the pedicle is minimized or prevented.

The outer surface 11 of the elongated tubular body 3 can be closed or sealed in the elongated direction E of extension of the elongated tubular body 3 between the proximal end 5 and the distal end 7, or entirely between the outer extremities 15, 23. The outer surface 11 or lateral outer surface of the elongated tubular body 3 is or defines an orifice-free surface or aperture-free surface.

An inner surface of the elongated body 3 may, for example, also comprise a flat or smooth surface or a surface without projections and/or depressions. This assures a smooth removal of the pedicle marker 1 along the length of a guide-wire GW and prevent or minimizes the risk of the guide-wire GW being removed with the pedicle marker 1.

The present disclosure also concerns a spinal instrument kit including or consisting solely of one or more pedicle markers 1. The spinal instrument kit can also include or consist solely of a pedicle boring or drilling tool, and/or a (Steffi) probe tool, and/or at least one Kirschner-wire.

The elements of the kit can be provided sterile and in sterile packaging. The elements of the KIT can be provided for single-use, or alternatively can be provided as multiple-use elements that can be re-sterilized in a hospital.

The present disclosure also concerns an orthopaedic method. The method can, for example, include the steps of:
   providing at least one or a plurality of pedicle markers 1,
   boring or creating a passage or elongated passage P into at least one pedicle or vertebra or a plurality of pedicles or vertebrae; and
   inserting the at least one or the plurality of pedicle markers 1 into the passage or passages P so that the at least one or each plug 9 closes or plugs the passage or passages P.

Figure 4:
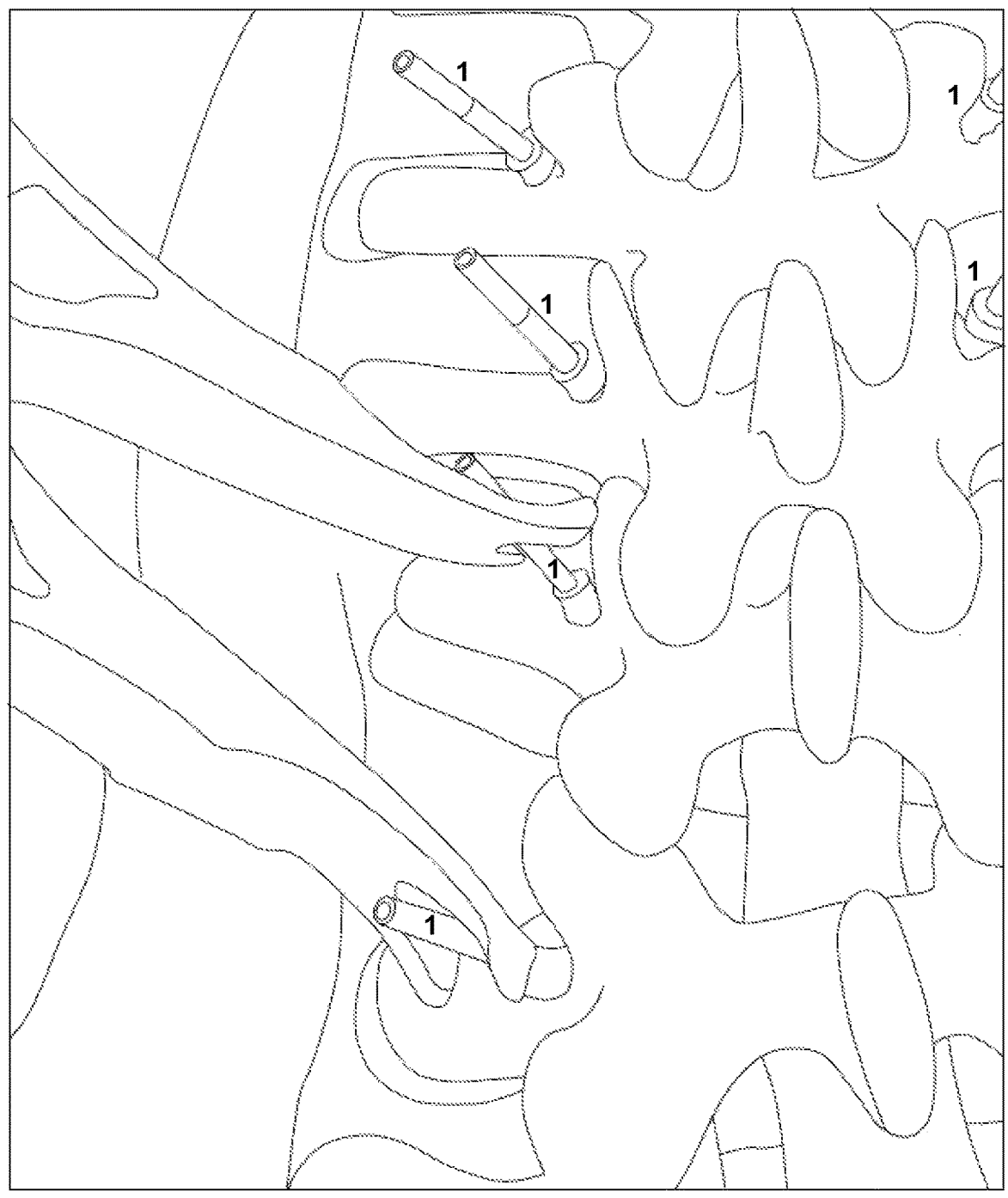
FIG. 4 shows an exemplary action that a Surgeon may carry out using the pedicle markers of the present disclosure.

A force can then be applied to the at least one or multiple pedicle markers 1 using a surgical tool, for example using a distractor to re-position or displace one or more vertebrae (see, for example, FIG. 4).

Alternatively or additionally, manual re-positioning can be carried out. Other actions necessary prior to insertion of the pedicle screws can additionally be carried out unhindered by the Surgeon. Such actions include but are not limited to decompression, spinal release, discectomy or interbody cage placement.

A spine cage can, for example, then be inserted or placed between vertebrae, or re-positioning of a spine cage between vertebrae can be carried out.

Figure 5:
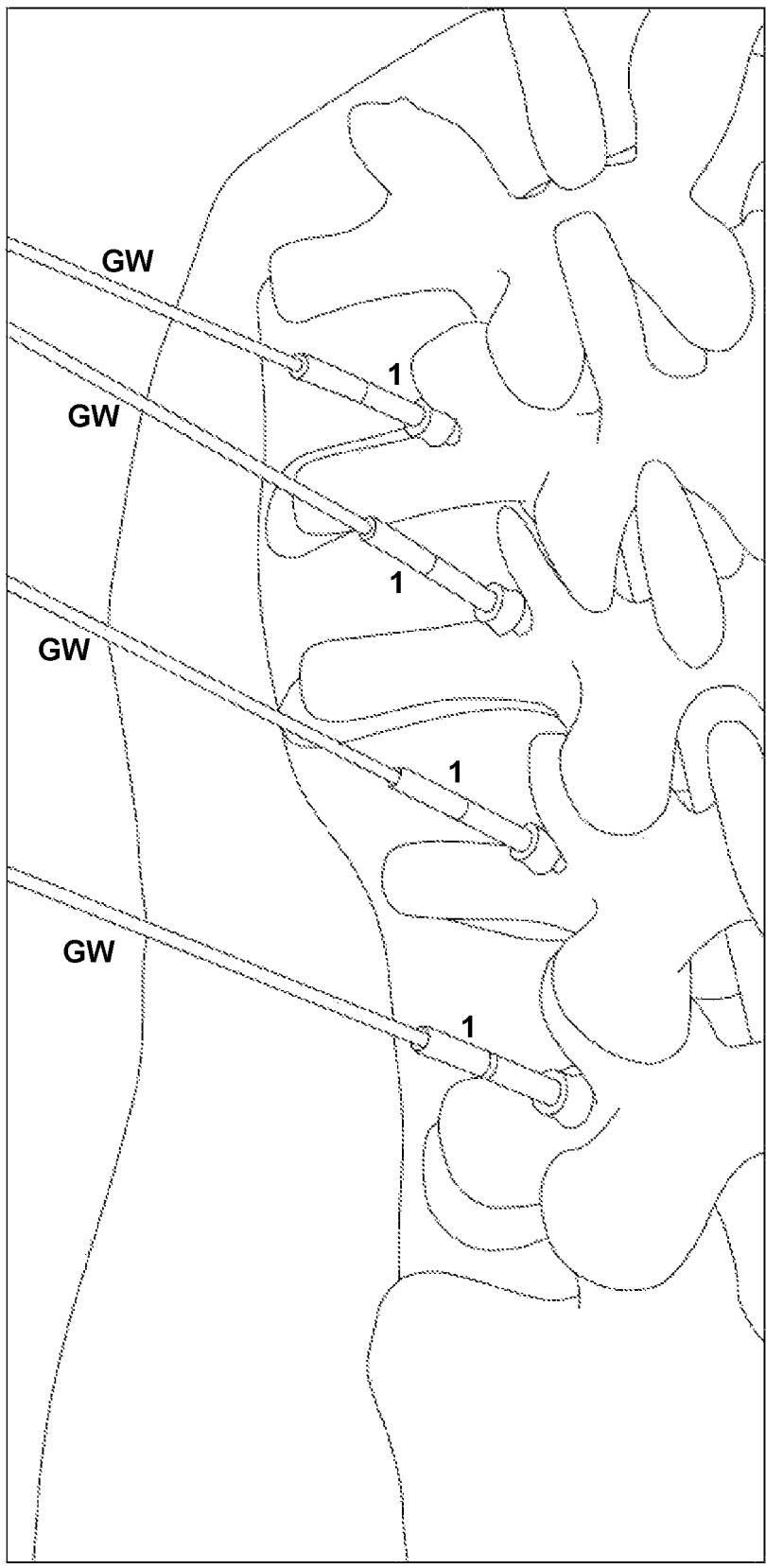
FIG. 5 shows a plurality of pedicle markers holding guide-wires and positioned in passages or bores present in pedicles.
Figure 6:
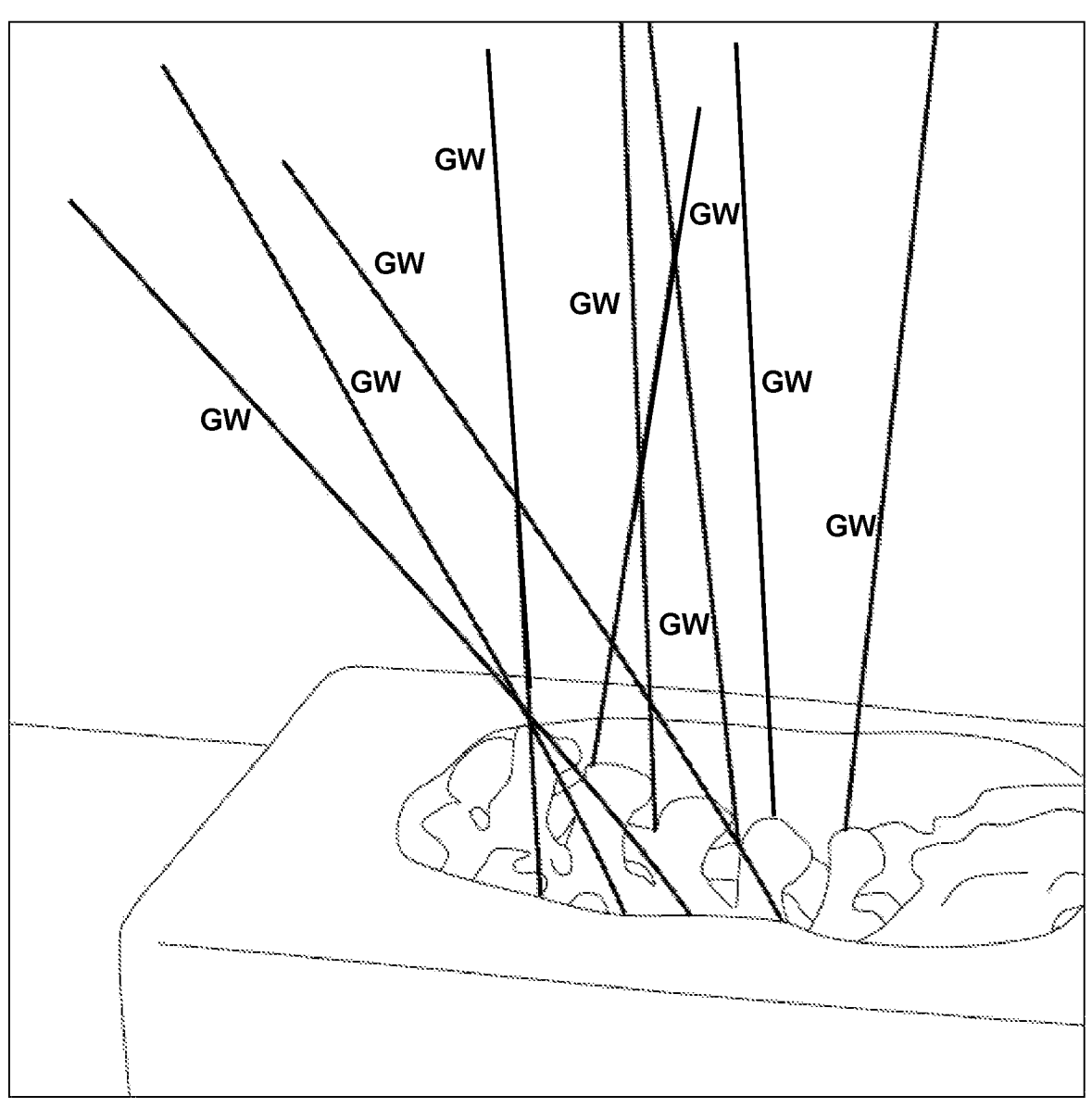
FIG. 6 shows the difficulty and hindrance faced by a Surgeon due the presence of guide-wires.

When the Surgeon is ready to insert the pedicle screws, a guide wire or Kirschner-wire GW can be inserted through the hollow passage 21 of one or the plurality of pedicle markers 1 and into the passage or passages P in the pedicles (see, for example, FIG. 5).

The pedicle markers 1 can then be removed by guiding them away from the pedicle and along the Kirschner-wire GW to remove the pedicle marker 1 from the patient.

The pedicle markers 1 also advantageously allows the K-wires to be inserted into the passage of the pedicle without bending of the K-wire GW due to the guiding function of the elongated body 3. The pedicle markers 1 further permit removal of the pedicle marker 1 without bending of the K-wire GW and without simultaneous pulling out of the k-wire.

Moreover, the pedicle markers 1 do not disrupt the Surgeon's current manner of operating on a patient but simply brings an additional option that renders the operation easier for the Surgeon.

The pedicle screw can then receive the guide-wire GW there-through and be guided along the wire GW to the passage P in the pedicle and inserted into the passage or bore P. This can be done for a plurality of pedicle screws.

While the invention has been disclosed with reference to certain preferred embodiments, numerous modifications, alterations, and changes to the described embodiments, and equivalents thereof, are possible without departing from the sphere and scope of the invention. The features of any one of the described embodiments may be included in any other of the described embodiments. The methods steps are not necessary carried out in the exact order presented above and can be carried out in a different order. Accordingly, it is intended that the invention not be limited to the described embodiments, and be given the broadest reasonable interpretation in accordance with the language of the appended claims.

The invention claimed is:

1. An orthopedic method comprising:
providing at least one pedicle marker each comprising:
an elongated tubular body comprising a proximal end configured to receive a guide-wire or a Kirschner-wire and a distal end through which the guide-wire or the Kirschner-wire is configured to exit, the elongated tubular body extending from the proximal end to the distal end, and
a plug enclosing the elongated tubular body, the plug being located at an extremity of the proximal end of the elongated tubular body of a respective one of the at least one pedicle marker, the plug comprising at least one groove or depression extending around a body of the plug and configured to receive a surgical tool when the respective one of the at least one pedicle marker is positioned in a respective pedicle screw passage formed in a respective pedicle,
the elongated tubular body including an external surface that is non-threaded at least from the plug to the distal end,
the plug being configured to temporarily seal the respective pedicle screw passage before a pedicle screw is positioned inside the respective pedicle screw passage in place of the respective one of the at least one pedicle marker,
the plug being attached immobile and non-displaceable on the elongated tubular body,
the plug being located at a distance from the distal end of the elongated tubular body of the respective one of the at least one pedicle marker, the plug being configured to seal the respective pedicle screw passage formed in the respective pedicle when a portion of the elongated tubular body extending between the distal end of the elongated tubular body and the plug is fully positioned inside the respective pedicle screw passage,
the plug further comprising
a distal section having a width or a diameter configured to seal or close the respective pedicle screw passage formed in the respective pedicle, and
a landing radially protruding outwards and away from the body of the plug, the landing being disposed between the distal section of the plug and the at least one groove or depression, the body of the plug extending to inwardly taper between the landing and the at least one groove or depression;
boring the respective pedicle screw passage into the respective pedicle;
inserting the respective one of the at least one pedicle marker into said respective pedicle screw passage so that the plug of the respective one of the at least one pedicle marker closes or plugs the respective pedicle screw passage; and
applying a force to the respective one of the at least one pedicle marker using a surgical tool or manually to re-position or displace the respective pedicle.

2. The orthopedic method according to claim 1, wherein the external surface of the elongated tubular body is non-threaded along an entire length of the elongated tubular body.

3. The orthopedic method according to claim 1, wherein the external surface of the elongated tubular body is closed or liquid-tight along an elongated direction of extension of the elongated tubular body between at least the plug and the distal end.

4. The orthopedic method according to claim 1, wherein the external surface of the elongated tubular body is closed or liquid-tight in an elongated direction of extension of the elongated tubular body between the proximal end and the distal end.

5. The pedicle-marker orthopedic method according to claim 1, wherein the external surface of the elongated tubular body is or defines an aperture-free surface.

6. The orthopedic method according to claim 1, wherein the plug further includes an upper section extending away from the at least one groove or depression and defining a channel configured to receive and guide the guide-wire or the Kirschner-wire.

7. The orthopedic method according to claim 1, wherein a tubular body passage through the elongated tubular body extends from the extremity of the proximal end to an outer extremity of the distal end.

8. The orthopedic method according to claim 1, further comprising:
carrying out one of: decompression, spinal release, discectomy, interbody cage placement, and re-positioning.

9. The orthopedic method according to claim 1, wherein the surgical tool is a distractor.

10. The orthopedic method according to claim 1, wherein the elongated tubular body includes a tubular body passage permitting the guide-wire or the Kirschner-wire to be received and guided through the elongated tubular body without bending of the guide-wire or the Kirschner-wire.

11. The orthopedic method according to claim 1, wherein the at least one groove or depression is an annular groove or depression.

12. The orthopedic method according to claim 1, wherein the landing radially protrudes outwards and away from the body of the plug to define an outermost radial extremity of the plug.

13. The orthopedic method according to claim 1, wherein the pedicle marker includes a plurality of pedicle markers, the respective pedicle screw passage includes a plurality of pedicle screw passages, the respective pedicle includes a plurality of pedicles, the plurality of pedicle screw passages is respectively bored into the plurality of pedicles, the plurality of pedicle markers is inserted into respective ones of the plurality of pedicle screw passages so that each of the plugs of the plurality of pedicle markers closes or plugs the respective ones of the plurality of pedicle screw passages, and the force is applied to at least two pedicle markers of the plurality of pedicle markers using the surgical tool or manually to re-position or displace the respective pedicles in which the at least two pedicle markers are inserted.

14. The orthopedic method according to claim 1, wherein the pedicle marker includes a plurality of pedicle markers, the respective pedicle screw passage includes a plurality of pedicle screw passages, the respective pedicle includes a plurality of pedicles, the plurality of pedicle screw passages is respectively bored into the plurality of pedicles, the plurality of pedicle markers is inserted into respective ones of the plurality of pedicle screw passages so that each of the plugs of the plurality of pedicle markers closes or plugs the respective ones of the plurality of pedicle screw passages, the guide-wire or the Kirschner-wire includes a plurality of guide-wires or a plurality of Kirschner-wires, the plurality of guide-wires or the plurality of Kirschner-wires is inserted through respective ones of the plurality of pedicle markers and into respective ones of the plurality of pedicle screw passages in respective ones of the plurality of pedicles, and the plurality of pedicle markers is guided away from the plurality of pedicles and along the respective guide-wires or the respective Kirschner-wires to remove the plurality of pedicle markers.

15. The orthopedic method according to claim 14, wherein the pedicle screw includes a plurality of pedicle screws, wherein the plurality of pedicle screws is guided along respective ones of the plurality of guide-wires or the plurality of Kirschner-wires and is inserted into the respective ones of the plurality of pedicle screw passages.

16. An orthopedic method comprising:

providing at least one pedicle marker each comprising:

an elongated tubular body comprising a proximal end configured to receive a guide-wire or a Kirschner-wire and a distal end through which the guide-wire or the Kirschner-wire is configured to exit, the elongated tubular body extending from the proximal end to the distal end, and a plug enclosing the elongated tubular body, the plug being located at an extremity of the proximal end of the elongated tubular body of a respective one of the at least one pedicle marker, the plug comprising at least one groove or depression extending around a body of the plug and configured to receive a surgical tool when the respective one of the at least one pedicle marker is positioned in a respective pedicle screw passage formed in a respective pedicle, the elongated tubular body including an external surface that is non-threaded at least from the plug to the distal end, the plug being configured to temporarily seal the respective pedicle screw passage before a pedicle screw is positioned inside the respective pedicle screw passage in place of the respective one of the at least one pedicle marker, the plug being attached immobile and non-displaceable on the elongated tubular body, the plug being located at a distance from the distal end of the elongated tubular body of the respective one of the at least one pedicle marker, the plug being configured to seal the respective pedicle screw passage formed in the respective pedicle when a portion of the elongated tubular body extending between the distal end of the elongated tubular body and the plug is fully positioned inside the respective pedicle screw passage, the plug further comprising a distal section having a width or a diameter configured to seal or close the respective pedicle screw passage formed in the respective pedicle, and a landing radially protruding outwards and away from the body of the plug, the landing being disposed between the distal section of the plug and the at least one groove or depression, the body of the plug extending to inwardly taper between the landing and the at least one groove or depression;

boring the respective pedicle screw passage into the respective pedicle;

inserting the respective one of the pedicle marker into said respective pedicle screw passage so that the plug of the respective one of the at least one pedicle marker closes or plugs the respective pedicle screw passage;

inserting a guide-wire or a Kirschner-wire through the respective one of the pedicle marker into said respective pedicle screw passage in the respective pedicle; and guiding the respective one of the pedicle marker away from the respective pedicle and along the guide-wire or the Kirschner-wire to remove the respective one of the pedicle marker.

17. The orthopedic method according to claim 16, further comprising:

guiding the pedicle screw along the guide-wire or the Kirschner-wire and inserting the pedicle screw into the respective pedicle screw passage.

* * * * *